United States Patent [19]

Richardson et al.

[11] Patent Number: 4,678,789

[45] Date of Patent: Jul. 7, 1987

[54] TRIAZOLE ANTIFUNGAL AGENTS

[75] Inventors: Kenneth Richardson; Peter J. Whittle, both of Canterbury, England

[73] Assignee: Pfizer Inc., New York, N.Y.

[21] Appl. No.: 479,525

[22] Filed: Mar. 28, 1983

[30] Foreign Application Priority Data

Apr. 7, 1982 [GB] United Kingdom ............... 82 10312

[51] Int. Cl.⁴ .................. C07D 401/12; C07D 403/12; C07D 417/12; A61K 31/41
[52] U.S. Cl. .................................. 514/262; 514/269; 514/312; 514/340; 514/363; 514/367; 514/369; 514/381; 514/384; 544/316; 544/319; 544/321; 544/265; 544/276; 546/153; 546/276; 548/141; 548/142; 548/166; 548/169; 548/136; 548/186; 548/231; 548/262; 548/265; 548/266
[58] Field of Search ............... 548/265, 266, 262, 186, 548/166, 169, 231, 136, 141, 142; 546/153, 276; 544/316, 321, 319, 276, 265; 514/262, 269, 312, 340, 363, 367, 369, 381, 384

[56] References Cited

U.S. PATENT DOCUMENTS 4,330,547 5/1982 Kraatz ................................ 424/263

FOREIGN PATENT DOCUMENTS 61835 10/1982 European Pat. Off. .

Primary Examiner—Robert Gerstl
Attorney, Agent, or Firm—Charles J. Knuth; Albert E. Frost; Peter C. Richardson

[57] ABSTRACT

Compounds of the general formula:

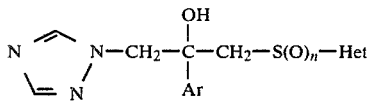

wherein Ar is naphthyl, biphenylyl, phenyl or substituted phenyl; n is 0, 1 or 2; and Het is a heterocyclic group which may optionally be substituted or fused to a phenyl, substituted phenyl or further heterocyclic ring; and their pharmaceutically acceptable salts are antifungal agents useful in combatting fungal infections in animals, including humans.

11 Claims, No Drawings

TRIAZOLE ANTIFUNGAL AGENTS

BACKGROUND OF THE INVENTION

This invention relates to novel triazole derivatives which have antifungal activity and are useful in the treatment of fungal infections in animals, including humans.

European patent application No. 82300888.3, published Oct. 6, 1982 as publication number 0061835, broadly describes a larger series of S- and O-ethers of 2-aryl-3-mercapto(or 3-hydroxy)-1-(1H-1,2,4-triazol-1-yl)propan-2-ols, and of the corresponding sulfoxides and sulfones of said mercapto derivatives, as antifungal agents.

Concurrently filed U.S. patent applications of Richardson and Gymer, entitled "Antifungal S-Ethers of 2-Aryl-3-Mercapto-1-(1H-1,2,4-Triazol-1-yl)Propan-2-Ols and Corresponding Sulfoxides and Sulfones", and of Richardson, Whittle and Cooper, entitled "Antifungal S-Arylmethyl- and S-Heterocyclylmethyl Ethers of 2-Aryl-3-Mercapto-1-(1H-1,2,4-Triazol-1-yl)Propan-2-Ols", and identified by Ser. Nos. 479,524 and 479,526, both filed 3/28/1983, respectively, are directed to related S-ethers of 2-aryl-3-mercapto-1-(1H-1,2,4-triazol-1-yl)propan-2-ols.

SUMMARY OF THE INVENTION

According to the invention, there are provided compounds of the formula:

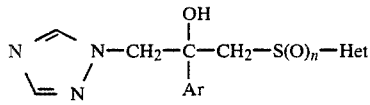   I wherein
Ar is naphthyl, biphenylyl, phenyl or substituted phenyl;
n is 0, 1 or 2; and
Het is a heterocyclic group which may optionally be substituted or fused to a phenyl, substituted phenyl or further heterocyclic ring;
and their pharmaceutically acceptable salts.

When Ar is a substituted phenyl group, it may be substituted by from 1 to 3 substituents, each substituent being independently halo, $CF_3$, $C_1$-$C_4$ alkyl, $C_1$-$C_4$ alkoxy or $C_1$-$C_4$ alkylthio. A preferred substituted phenyl group Ar is dihalophenyl, especially 2,4-dichlorophenyl. The preferred biphenyl group is para-biphenyl.

"Halo" means F, Cl, Br or I.

Heterocyclic groups include 5 and 6 membered aromatic heterocyclic groups linked to the $S(O)_n$ group via a ring carbon atom. Particular examples include 2-imidazolyl, 2-thiazolyl, 3-(1,2,4-triazolyl), 5-tetrazolyl, 2-(1,3,4-thiadiazolyl), 2-, 3- and 4-pyridyl and 2- and 4-pyrimidinyl as well as benzo fused systems such as quinolyl and benzothiazolyl and biheterocyclic systems such as purinyl. Substituents for the heterocyclic or fused phenyl ring include one or more halo, $CF_3$, $C_1$-$C_4$ alkyl, $C_1$-$C_4$ alkoxy, amino, mono or di $C_1$-$C_4$ alkyl amino, alkanoylamino, hydroxy or thio groups.

Preferred heterocyclic groups include imidazolyl, pyrimidinyl and thiazolyl, especially 2-imidazolyl, 2-(1-methyl-imidazolyl), 3-(1,2,4-triazolyl), 2-thiazolyl, 2- and 4-pyrimidinyl, and 2-(4,5-dimethylthiazolyl). Preferred values of Ar are halophenyl, especially 2,4-dichlorophenyl.

Alkyl, alkoxy and alkanoyl groups may be straight or branched chain where appropriate.

The invention also provides a pharmaceutical composition comprising a compound of the formula (I) or a pharmaceutically acceptable salt thereof, together with a pharmaceutically acceptable diluent or carrier.

The invention further provides a compound of the formula (I) or a pharmaceutically acceptable salt thereof, for use in treating fungal infections in animals, including humans.

DETAILED DESCRIPTION OF THE INVENTION

The compounds of formula (I) can be obtained by a number of different processes according to the invention.

(1) In one process, the compound of the formula (I) in which n is 0 can be prepared from an oxirane of the formula:

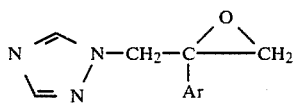   II by reaction with a heterocyclic thiol of the formula:

Het—SH   III wherein Ar and Het are as previously defined.

The reaction can be achieved under a variety of different conditions, depending to some extent on the precise nature of the reactants. Generally it is possible to achieve the reaction in a convenient manner by simply heating the oxirane (II), as its free base, with excess of the heterocyclic thiol (III) in an organic solvent, e.g. dioxan. A period of up to three days at reflux temperature is generally sufficient; however, addition of a catalytic amount of dilute sodium hydroxide solution often gives improved yields and reduces reaction times. The product can be isolated and purified by conventional procedures; for example, by evaporating the solvent, taking the product up in a water immiscible organic solvent, extracting the product with dilute sodium hydroxide or potassium carbonate solution to remove unreacted thiol, drying and evaporating the solvent. The product may be further purified, if desired, by crystallization or by chromatography.

As an alternative procedure, the oxirane as its methanesulphonate salt and the heterocyclic thiol are heated together in an organic solvent, e.g. N,N-dimethylformamide or tetrahydrofuran, in the presence of a base, e.g. potassium carbonate or sodium hydride. A temperature of from 60° to 80° C. is generally employed, and under these conditions, the reaction is generally substantially complete within a few hours. The product is isolated and purified as previously described.

As a further variation the oxirane as its methanesulphonate salt is heated with excess of the heterocyclic thiol under reflux in glacial acetic acid for a period of several hours.

The oxiranes (II) can be obtained by conventional methods, typically from the corresponding ketones (IV):

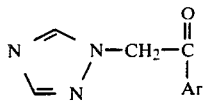

by reaction with dimethyloxosulphonium methylide prepared from trimethylsulphoxonium iodide and either sodium hydride in dimethylsulphoxide or using cetrimide and sodium hydroxide in a mixture of water and toluene.

The reaction using sodium hydride is typically achieved by adding dry powdered trimethylsulphoxonium iodide to a suspension of sodium hydride in dimethylsulphoxide. After stirring for, say, 30 minutes at room temperature, the ketone (IV) is added in an approximately equimolar amount in dimethylsulphoxide. The reaction mixture may be warmed to accelerate the reaction and after several hours at 50°–80° C., the product can be isolated by conventional procedures.

The reaction utilizing cetrimide is typically achieved by stirring the ketone (IV), trimethylsulphoxonium iodide and cetrimide vigorously together in a mixture of toluene and sodium hydroxide solution for about an hour at up to about 100° C. The oxirane product can then be isolated by conventional procedures.

When Ar is a phenyl group containing no ortho substituent, or is biphenylyl, the cetrimide route should be used.

The ketones (IV) are either known compounds or can be prepared by procedures analogous to those of the prior art. The preparation of 2-(1H-1,2,4-triazol-1-yl)-2',4'-dichloroacetophenone from 2-bromo-2',4'-dichloroacetophenone, 1,2,4-triazole and potassium carbonate is, for example, described in Example 1 of British Patent Specification No. 1512918, which utilizes acetonitrile as the solvent under reflux for 20 hours. We have found that this type of reaction is generally best carried out in acetone at 0°–20° C., when it is generally complete in a shorter period of time, e.g. 4 hours or less.

The heterocyclic thiols of formula III are generally known compounds or they are prepared from readily available starting materials by conventional reactions.

(2) The compounds of the formula (I) in which n is 1 (sulphoxides) and 2 (sulphones) can be prepared by the controlled or strong oxidation, respectively, of the corresponding compounds in which n is 0. The compounds in which n is 2 can also be prepared by the oxidation of the compounds in which n is 1.

The preferred oxidizing agent is m-chloroperbenzoic acid: approximately one equivalent should be used to prepare the sulphoxides and an excess to prepare the sulphones.

In a typical procedure involving the preparation of a sulphoxide, the corresponding thio compound is dissolved in a mixture of isopropanol and chloroform (1:1, v/v), and the solution is cooled to below 5° C. in an ice bath. Slighly less than 1 equivalent of m-chloroperbenzoic acid is added in portions over a few minutes. The mixture is then stirred for about two hours. If thin layer chromatography indicates unreacted starting material, a small further quantity of m-chloroperbenzoic acid (up to 1 equivalent) is added. The sulphoxides have two asymmetric centres and thus exist in two diastereoisomeric forms. Thus, the sulphoxide product of the oxidation, which can be isolated by conventional procedures, will be a mixture of the two diastereoisomers. If desired, the diastereoisomers can be separated by column chromatography, e.g. on silica, since they usually differ in polarity. The sulphones can be obtained simply by adding excess m-chloroperbenzoic acid to a solution of the crude sulphoxide, and stirring for a few hours, at room temperature. Alternatively, the sulphones can be prepared by the oxidation of the thio compounds (n=0) using excess m-chloroperbenzoic acid.

(3) In the case where the heterocyclic group or the fused phenyl ring contain substituted groups, conventional chemical transformation reactions can be used to prepare simple derivatives and related compounds.

Thus, for example, when the heterocyclic ring contains an amino group, a conventional acetylation reaction (e.g. using acetic anhydride in pyridine) may be employed to prepare the N-acetyl derivative. Other transformation reactions and the conditions required for their performance will be well known to those skilled in the art.

The sulphoxides of the formula (I) where n=1, have two asymmetric centres, namely, the carbon atom bearing the hydroxy group and the sulphoxide sulphur atom. Consequently, the sulphoxides exist in two diastereoisomeric forms, each of which is a racemate consisting of a pair of enantiomers. The two diastereoisomeric pairs can be readily separated by column chromatography, since they differ markedly in polarity. Each diastereoisomeric pair can be resolved further into its individual optically active enantiomers by techniques known to those skilled in the art. In some cases, one diastereoisomeric pair may predominate over the other. The invention includes each diastereoisomeric pair whether resolved or not.

All the compounds of the invention contain at least one chiral centre, and the invention includes both resolved and unresolved forms.

Pharmaceutically acceptable acid addition salts of the compounds of the formula (I) include those formed from strong acids which form non-toxic acid addition salts, such as hydrochloric, hydrobromic, sulphuric, nitric, oxalic and methanesulphonic acids.

The salts can be obtained by conventional procedures, e.g. by mixing solutions containing equimolar amounts of the free base and desired acid, and the required salt is collected by filtration, if insoluble, or by evaporation of the solvent.

The compounds of the formula (I) and their pharmaceutically acceptable salts are anti-fungal agents, useful in combating fungal infections in animals, including humans. For example, they are useful in treating topical fungal infections in man caused by, among other organisms, species of Candida, Trichophyton, Microsporum, or Epidermophyton, or in mucosal infections caused by *Candida albicans* (e.g. thrush and vaginal candidiasis). They can also be used systemically in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the anti-fungal activity of the compounds can be performed by determining the minimum inhibitory concentration (m.i.c.) of the test compounds in a suitable medium at which growth of the particular micro-organism fails to occur. In practice, a series of agar plates, each having the test compound incorporated at a particular concentration are inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Crypotococcus neoformans, Aspergillus fumigatus,* Trichophyton spp; Microsporum spp; *Epidermophyton floccosum, Coccidioides immitis,* and *Torulopsis glabrata.*

The in vivo evaluation of the compounds can be carried out at a series of dose levels by intaperitoneal or intravenous injection or by oral administration, to mice which are inoculated with a strain of *Candida albicans.* Activity is based on the survival of a treated group of mice after the death of an untreated group of mice following 48 hours observation. The dose level at which the compound provides 50% protection against the lethal effect of the infection is noted.

For human use, the anti-fungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or supensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, it is expected that the daily dosage level of the anti-fungal compounds of the formula (I) will be from 0.1 to 10 mg/kg (in divided doses) when administered by either the oral or parenteral route. Thus, tablets or capsules of the compounds can be expected to contain from 5 mg to 0.5 g of active compound for administration singly or two or more at a time as appropriate. The physician, in any event, will determine the actual dosage which will be most suitable for an individual patient, and it will vary with the age, weight and response of the particular patient. The above dosages are exemplary of the average case. There can, of course, be individual instances where higher or lower dosage ranges are merited, and such are within the scope of this invention.

Alternatively, the anti-fungal compounds of formula (I) may be administered in the form of a suppository or pessary, or they may be applied topically in the form of a lotion, solution, cream, ointment or dusting powder. For example, they may be incorporated into a cream consisting of an aqueous emulsion of polyethylene glycols or liquid paraffin; or they may be incorporated, at a concentration between 1 and 10%, into an ointment consisting of a white wax or white, soft paraffin base together with such stabilizers and preservatives as may be required.

The compounds are also useful as agricultural fungicides for treating plants and seeds to eradicate or prevent fungal infections.

The following Examples illustrate the invention:

EXAMPLE 1

1-[2-(2,4-Dichlorophenyl)-2-hydroxy-3-(1,2,4-triazol-3-ylthio)-propyl]-1,2,4-triazole 2-(2,4-Dichlorophenyl)-2-(1H-1,2,4-triazol-1-ylmethyl)oxirane methanesulphonte salt (5 g, 0.0137 m), 3-mercapto-1,2,4-triazole (5 g, 0.05 m), and anhydrous potassium carbonate (14 g, 0.1 m) were stirred in dry N,N-dimethylformamide (100 ml) at 80° C. for 1 hour. The solvent was then evaporated and the residue was dissolved in water and extracted with methylene chloride. The combined extracts were washed once with dilute sodium bicarbonate solution, dried (MgSO$_4$), and evaporated to give a solid residue which was recrystallized from isopropanol/water to give the title compound, 3.7 g (74%); m.p. 180°–182° C.

Analysis %: Found: C, 42.29; H, 3.30; N, 22.86; $C_{13}H_{12}N_6OSCl_2$ requires: C, 42.07; H, 3.26; N, 22.64%.

EXAMPLE 2

1-[2-(2,4-Dichlorophenyl)-2-hydroxy-3-(1-methylimidazol-2-ylthio)-propyl]-1,2,4-triazole 2-(2,4-Dichlorophenyl)-2-(1H-1,2,4-triazol-1-ylmethyl)-oxirane (0.27 g, 0.001 m), and 2-mercapto-1-methylimidazole (0.228 g, 0.002 m) were heated under reflux in dioxan for 72 hours. The dioxan was then evaporated and the residue was dissolved in ethyl acetate (70 ml). This solution was washed sequentially with dilute potassium carbonate solution, dilute sodium hydroxide solution, and water dried (MgSO$_4$) and evaporated to give an oil which crystallized on standing. Recrystallization from ethyl acetate/hexane gave the title compound 0.252 g (66%); m.p. 159°–161° C.

Analysis %: Found: C, 46.97; H, 3.84; N, 18.62; $C_{15}H_{15}N_5OSCl_2$ requires: C, 46.88; H, 3.93; N, 18.23%.

EXAMPLE 3

1-[2-(2,4-Dichlorophenyl)-2-hydroxy-3-(thiazol-2-ylthio)propyl]-1,2,4-triazole 2-(2,4-Dichlorophenyl)-2-(1H-1,2,4-triazol-1-ylmethyl)oxirane, methanesulphonate salt, (6 g, 0.0164 m) and 2-mercaptothiazole (6 g, 0.05 m) were heated in glacial acetic acid (200 ml) under refluxed for 4 hours. The solvent was then evaporated and the residue was basified with dilute sodium hydroxide solution and extracted with methylene chloride. The extract was washed once with dilute sodium hydroxide solution, dried (MgSO$_4$) and evaporated to give a pale brown glass (5.4 g) which was chromatographed on silica, eluting with ethyl acetate:ether:methanol:diethylamine 25:75:2:2, to give, after one recrystallization from isopropanol, the title compound 2 g, (32%); m.p. 110°–111° C.

Analysis %: Found: C, 43.36; H, 3.12; N, 14.83; $C_{14}H_{11}N_4OS_2Cl_2$ requires: C, 43.43; H, 3.12; N, 14.47%.

EXAMPLES 4-21

The following compounds were prepared by the general procedures described in Examples 1 to 3 but using the appropriate heterocyclic thiol as reactant.

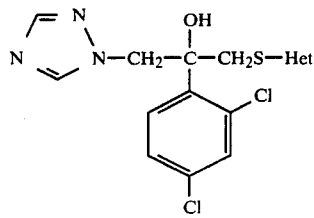

| Example No. | Het | m.p. °C. | Analysis (Theoretical in brackets) | | |
|---|---|---|---|---|---|
| | | | C | H | N |
| 4 | ![N/NH imidazole] | 231-232 | 45.44 (45.42 | 3.56 3.54 | 18.97 18.92) |
| 5 | ![4,5-dimethylthiazole] (1) | 175-185 | 39.14 (39.34 | 3.78 3.69 | 11.34 11.47) |
| 6 | ![5-chlorobenzothiazole] | 148-150 | 46.01 (45.81 | 2.67 2.76 | 12.36 11.88) |
| 7 | ![1-methyltetrazole] (3) | 78-81 | 41.45 (41.44 | 3.48 3.49 | 24.93 24.83) |
| 8 | ![4-amino-triazole-NH] (2) | 78-82 | 34.4 (34.71 | 2.74 2.91 | 20.53 20.61) |
| 9 | ![thiadiazole] | 156-159 | 39.99 (40.21 | 2.88 2.86 | 18.23 18.04) |
| 10 | ![thiadiazole-SH] | 200-202 | 37.6 (37.14 | 2.68 2.62 | 16.98 16.67) |
| 11 | ![7-CF3-quinoline] | 172-174 | 50.24 (50.50 | 2.97 3.01 | 10.86 11.22) |
| 12 | ![pyrimidine] (1) | 110-120 | 39.46 (39.56 | 3.28 3.3 | 15.25 15.3) |

-continued
EXAMPLES 4-21
The following compounds were prepared by the general procedures described in Examples 1 to 3 but using the appropriate heterocyclic thiol as reactant.
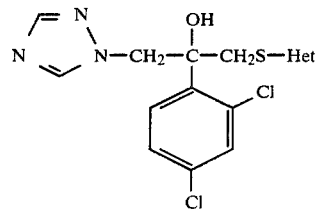
| Example No. | Het | m.p. °C. | Analysis (Theoretical in brackets) | | |
|---|---|---|---|---|---|
| | | | C | H | N |
| 13 | [pyrazine-CH2-] | 129–130 | 46.67 (47.14 | 3.33 3.43 | 18.72 18.32) |
| 14 | [bromopyrazine] | 151–152 | 39.45 (39.07 | 2.64 2.62 | 15.54 15.19) |
| 15 | [methylpyrimidine] | 94–98 | 41.04 (40.96 | 3.65 3.65 | 14.98 14.93) |
| 16 | [aminothiadiazole] | 192–194 | 38.38 (38.71 | 3.01 2.99 | 21.07 20.84) |
| 17 | [pyridyl] | 130–133 | 50.53 (50.40 | 3.68 3.70 | 15.29 14.69) |
| 18 | [pyridyl] | 126–128 | 50.29 (50.40 | 3.62 3.70 | 15.31 14.69) |
| 19 | [aminopurine] | 262–265 | 43.14 (43.03 | 3.26 3.36 | 25.26 25.11) (4) |
| 20 | [purine] | 229–234 (decomp.) (5) | 45.22 (45.49 | 3.59 3.08 | 21.94 23.22) |

EXAMPLES 4-21

The following compounds were prepared by the general procedures described in Examples 1 to 3 but using the appropriate heterocyclic thiol as reactant.

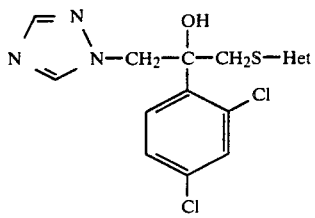

| Example No. | Het | m.p. °C. | Analysis (Theoretical in brackets) | | |
|---|---|---|---|---|---|
| | | | C | H | N |
| 21 | ![structure with N, N, CH₂CH₂CH₃] | 100 approx. (5) | 43.77 (45.5 | 4.50 4.49 | 15.07 15.61) |

(1) isolated as dihydrochloride
(2) isolated with 0.75 mole of chloroform
(3) isolated with 2% toluene present
(4) hemihydrate
(5) hygroscopic

EXAMPLE 22

1-[3-(2-Acetamido-1,3,4-thiadiazol-5-ylthio)-2-(2,4-dichlorophenyl)-2-hydroxy-propyl]-1,2,4-triazole 1-[3-(2-Amino-1,3,4-thiadiazol-5-ylthio)-2-(2,4-dichlorophenyl)-2-hydroxy-propyl]-1,2,4-triazole (0.5 g, 0.00124 m) was stirred at room temperature with a mixture of acetic anhydride (0.5 ml) and pyridine (5 ml) for one hour. The resulting solid was collected by filtration, washed with water and dried to give the title compound, 0.44 g (80%); m.p. 132° C.

Analysis %: Found: C, 39.78; H, 3.39; N, 18.82; $C_{15}H_{14}N_6OS_2Cl_2$ requires: C, 39.65; H, 3.32; N, 18.49.

EXAMPLE 23

1-[2-(2,4-Dichlorophenyl)-2-hydroxy-3-(1-methyl-imidazol-2-ylsulphinyl)-propyl]-1,2,4-triazole 1-[2-(2,4-Dichlorophenyl)-2-hydroxy-3-(1-methylimidazol-2-yl-thio)-propyl]-1,2,4-triazole (250 mg; 0.65 mM) was dissolved in a mixture of methylene chloride (7 ml) and isopropanol (7 ml). The solution was stirred and cooled in ice. To this solution was added metachloroperbenzoic acid (85% pure; 132 mg; 0.65 mM) in three portions over a period of ten minutes. The reaction was allowed to proceed for 18 hours at room temperature. Methylene chloride (100 ml) was added and the organic layer separated and washed with a solution of sodium carbonate (2.5 g) and sodium metabisulphite (2.5 g) in water (100 ml). The organic layer was then dried over magnesium sulphate and evaporated to give an oil containing the product as a mixture of the two sulphoxide diastereomers. The compounds were separated by chromatography on silica, eluting with a mixture of ethyl acetate, methanol and concentrated ammonium hydroxide (80:20:1) to yield a major product, Rf 0.40 (silica, ethylacetate:methanol:ammonium hydroxide, 80:20:1) which was recrystallized from ethyl acetate/hexane to give the title compound as isomer 1 (140 mg, 54%) m.p. 175°-178° C. (dec.).

Analysis %: Found: C, 44.89; H, 3.87; N, 17.80; $C_{15}H_{15}N_5O_2SCl_2$ requires: C, 45.01; H, 3.78; N, 17.50.

Further elution yielded a minor component, Rf 0.27 (same system), which was recrystallized from ethyl acetate/hexane to give the title compound as isomer 2 (60 mg, 23%) m.p. 162°-164° C.

Analysis %: Found: C, 45.11; H, 3.69; N, 17.19; $C_{15}H_{15}N_5O_2SCl_2$ requires: C, 45.01; H, 3.78; N, 17.50.

EXAMPLE 24

1-[2-(2,4-Dichlorophenyl)-2-hydroxy-3-(4,5-dimethyl-thiazol-2-yl-sulphinyl)propyl]-1,2,4-triazole The procedure of Example 23 was followed but starting with 1-[2-(2,4-dichlorophenyl)-2-hydroxy-3-(4,5-dimethyl-thiazol-2-ylthio)propyl]-1,2,4-triazole (250 mg) to yield the title sulphoxide (isomer 1) 20 mg 8%; m.p. 199°-200° C.

Analysis %: Found: C, 44.47; H, 3.67; N, 13.02; $C_{16}H_{16}N_4OS_2Cl_2$ requires: C, 44.55; H, 3.71; N, 12.99.

EXAMPLE 25

The following illustrate pharmaceutical compositions for the treatment of fungal infections:

(1) Capsule: 71 parts by weight of the compound of Example 3 are granulated with 3 parts maize starch and 22 parts lactose and then a further 3 parts of maize starch and 1 part magnesium stearate are added. The mixture is regranulated and filled into hard gelatin capsules.

(2) Cream: 2 parts by weight of the compound of Example 3 are dissolved in 10 parts of propylene glycol and mixed into 88 parts of a vanishing cream base.

(3) Pessary: 2 parts by weight of the compound of Example 3 are suspended in 98 parts of a warm liquified suppository base which is poured into moulds and allowed to solidify.

PREPARATION 1

Preparation of 2-(2,4-Dichlorophenyl)-2-(1H-1,2,4-triazol-1-ylmethyl)-oxirane Sodium hydride (3.78 g, 0.079 mole as 50% dispersion in oil) was suspended, with stirring, in 20 ml of dry diethyl ether. The ether was then removed by decantation, and the sodium hydride was dried in a stream of dry nitrogen. 100 Ml of dry dimethyl sulphoxide was added followed by 17.34 (0.079 mole) of dry powdered trimethylsulphoxonium iodide, in portions, over 15 minutes. The resulting mixture was stirred for 30 minutes at room temperature (20° C.). 2-(1H-1,2,4-Triazol-1-yl)-2',4'-dichloro acetophenone (18.33 g, 0.072 Mole) as a solution in 50 ml of dry dimethyl sulphoxide was then added. The mixture was heated at 60° C. for 3 hours and allowed to stand at room temperature overnight. The reaction mixture was cooled and quenched in ice. The product was then extracted into ethyl acetate (600 ml). The ethyl acetate layer was separated, dried over magnesium sulphate, and concentrated to give a red gum. Column chromatography of the gum on silica, eluting with ether, gave 6.62 g (34.4%) of the title compound as a gum.

I claim:

1. A compound of the formula:

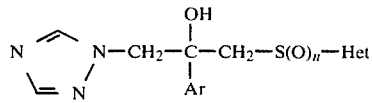

wherein
Ar is 2,4-dichlorophenyl;
n is 0, 1 or 2; and
Het is 2-imidazolyl, 2-thiazolyl, 3-(1,2,4-triazolyl), 5-tetrazolyl, 2-(1,3,4-thiadiazolyl), 2-, 3- or 4-pyridyl, 2- or 4-pyrimidinyl, quinolyl, benzothiazolyl or purinyl, each being optionally mono- or di-substituted by halo, $CF_3$, $C_1$-$C_4$ alkyl, amino, alkanoylamino or thio groups; and their pharmaceutically acceptable salts.

2. A compound as claimed in claim 1 wherein Het is 2-imidazolyl, 2-(1-methyl-imidazolyl), 2-thiazolyl, 2-pyrimidinyl or 4-pyrimidinyl.

3. A compound as claimed in claim 2 wherein n is 0.

4. The compound as claimed in claim 3 wherein Het is 2-(1-methyl-imidazolyl).

5. A compound as claimed in claim 2 wherein n is 1.

6. The compound as claimed in claim 5 wherein Het is 2-(1-methyl-imidazolyl).

7. The compound as claimed in claim 3 wherein Het is 2-thiazolyl.

8. The compound as claimed in claim 3 wherein Het is 2-imidazolyl.

9. The compound as claimed in claim 3 wherein Het is 4-pyrimidinyl.

10. An antifungal pharmaceutical composition comprising a compound as claimed in claim 1, or a pharmaceutically acceptable salt thereof, together with a pharmaceutically acceptable diluent or carrier.

11. A method of treating a fungal infection in a human which comprises administering to said human an antifungal amount of a compound according to claim 1.

* * * * *